(12) United States Patent
Betageri

(10) Patent No.: US 6,759,058 B1
(45) Date of Patent: Jul. 6, 2004

(54) ENTERIC-COATED PROLIPOSOMAL FORMULATIONS FOR POORLY WATER SOLUBLE DRUGS

(75) Inventor: Guru V. Betageri, Chino Hills, CA (US)

(73) Assignee: Western Center for Drug Development College of Pharmacy Western University of Health Sciences, Pomona, CA (US)

(*) Notice: Subject to any disclaimer, the term of this patent is extended or adjusted under 35 U.S.C. 154(b) by 0 days.

(21) Appl. No.: 09/931,399

(22) Filed: Aug. 16, 2001

Related U.S. Application Data

(60) Provisional application No. 60/286,386, filed on Apr. 25, 2001.

(51) Int. Cl.[7] ............................ A61K 9/127; A61K 9/14
(52) U.S. Cl. ........................ 424/450; 424/489; 424/490; 424/494; 424/497
(58) Field of Search ................................ 424/450, 1.21, 424/9.321, 9.51, 417, 475–482, 451, 452, 455, 463, 464, 489–502, 94.3, 812; 436/829; 935/54

(56) References Cited

U.S. PATENT DOCUMENTS

| | | | |
|---|---|---|---|
| 4,615,885 A | * | 10/1986 | Nakagame |
| 4,849,227 A | | 7/1989 | Cho |
| 5,206,219 A | * | 4/1993 | Desai |
| 5,505,967 A | | 4/1996 | Geary et al. |
| 5,635,206 A | * | 6/1997 | Ganter |
| 5,665,700 A | | 9/1997 | Cho et al. |
| 5,888,550 A | | 3/1999 | Cook et al. |
| 6,156,731 A | | 12/2000 | Grass et al. |
| 6,187,335 B1 | | 2/2001 | Brey et al. |
| 6,309,663 B1 | | 10/2001 | Patel et al. |

FOREIGN PATENT DOCUMENTS

EP          00 87993       *   9/1983

OTHER PUBLICATIONS

Chung SJ, *Future drug delivery research in South Korea*, J Control Release, Nov. 1, 1999; 62 (1–2): 73–79. Abstract in two pages.
Deo MR, Sant VP, Parekh SR, Khopade AJ, Banakar UV, *Proliposome–based transdermal delivery of levonorgestrel*, J Biomater Appl, Jul. 1997; 12(1): 77–88. Abstract in one page.
Perrett S, Golding M, Williams WP, *A simple method for the preparation of liposomes for pharmaceutical applications: characterization of the liposomes*, J Pharm Pharmacol, Mar. 1991; 43(3): 154–161. Abstract in one page.
Katare OP, Vyas SP, Dixit VK, *Effervescent granule based proliposomes of ibuprofen*, J Microencapsul, Oct.–Dec. 1990; 7(4): 455–62. Abstract in one page.
Hongming Chen, Vladimir Torchilin and Robert Langer, *Lectin–bearing Polymerized Liposomes as Potential Oral Vaccine Carriers*, , Pharmaceutical Research, vol. 13, No. 9, 1996, pp. 1378–1383.

(List continued on next page.)

Primary Examiner—Gollamudi S. Kishore
(74) Attorney, Agent, or Firm—Knobbe, Martens, Olson & Bear, LLP

(57) ABSTRACT

This invention relates to enteric-coated proliposomal formulations for oral medicaments. In particular, it relates to an enteric-coated proliposomal oral drug delivery system for poorly water soluble drugs and methods for making the same. The drug delivery system comprises a pharmaceutical agent, a phospholipid and an enteric coating material. The present invention provides enhanced stability and bioavailability for orally administered drugs.

10 Claims, 2 Drawing Sheets

OTHER PUBLICATIONS

P. Dufour, J.C. Vuillemard, E. Laloy and R.E. Simard, *Characterization of enzyme immobilization in liposomes prepared from proliposomes*, J. Microencapsulation, 1996, vol. 13, No. 2, pp. 185–194.

Byung–nak ahn, Shin–Keun, Kim and chang–Koo Shim, *Preparation and evaluation of proliposomes containing propranolol hydrochloride*, J. Microencapsulation, 1995, No. 4, pp. 363–375.

O.P. Katare, S.P. Vyas and V.K. Dixit, *Enhanced in vivo performances of liposomal Indomethacin derived from effervescent granule based proliposomes*, J. Microencapsulation, 1995, vol. 12, No. 5, pp. 487–193.

Nicholas I. Payne, Peter Timmins, Cheryl V. Ambrose, Michael D. Ward and Frank Ridgway, *Proliposomes: A Novel Solution to an Old Problem*, Journal of Pharmaceutical Sciences, Apr. 1986, vol. 75, No. 4, pp. 325–329.

Nicholas I. Payne, Ivan Browning and Cheryl A. Hynes, *Characterization of Proliposomes*, Journal of Pharmaceutical Sciences, 1986, 75(4): 330–332. Abstract in one page.

Poster presented by Dr. Guru Betageri at the American Association of Pharmaceutical Scientists Meeting in Indianapolis in Nov. 2000.

\* cited by examiner-

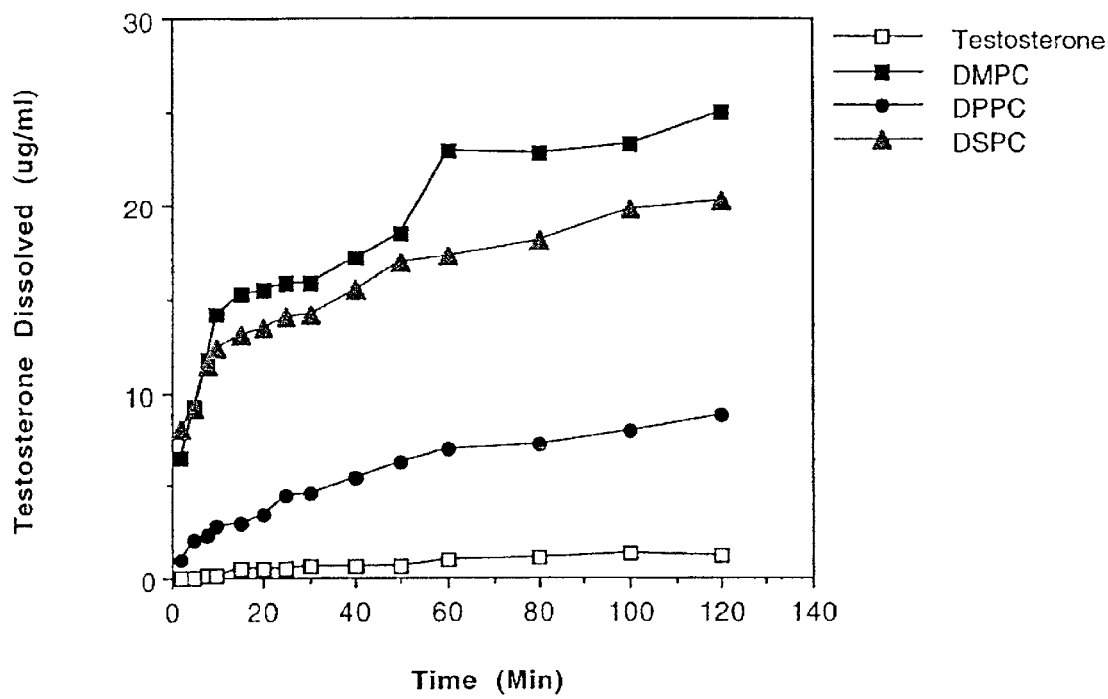
FIGURE ONE (1)

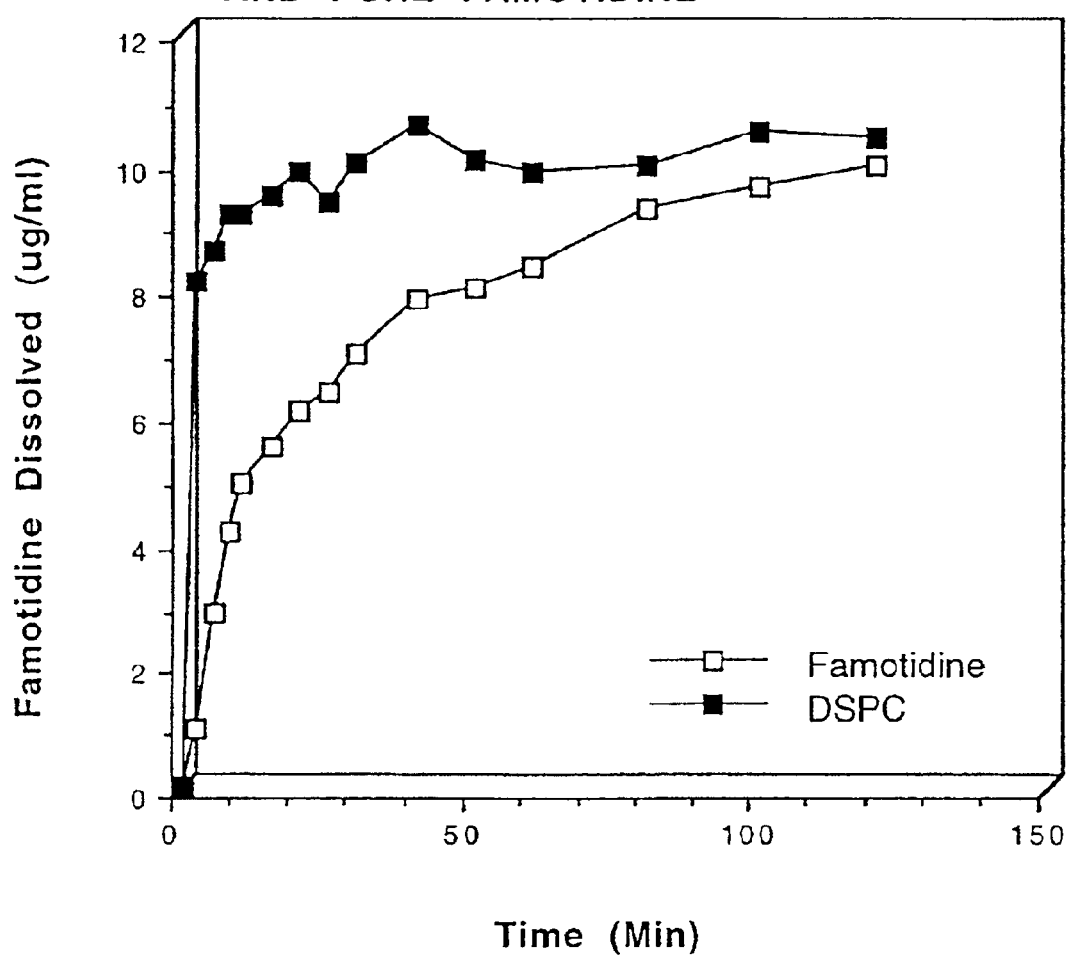
FIGURE TWO (2)

ENTERIC-COATED PROLIPOSOMAL FORMULATIONS FOR POORLY WATER SOLUBLE DRUGS

RELATED APPLICATIONS

This application claims benefit to U.S. Provisional Application No. 60/286,386, filed April 25, 2001, the entire teachings of which are incorporated herein by reference.

BACKGROUND OF THE INVENTION

1. Field of the Invention

This invention relates to enteric-coated proliposomal formulations for oral medicaments. In particular, it relates to enteric-coated proliposomal formulations for poorly water soluble drugs.

2. Description of the Related Art

Among the various routes of drug administration, the oral route is preferred because of its versatility, safety and patient comfort. The encapsulation of pharmaceuticals in liposomes is useful in reducing toxicity and improving the therapeutic effectiveness of certain drugs. For example, compounds such as insulin, factor VIII, tryptophan, phenylalanine, heparin, vitamin K etc., have been investigated for their effectiveness orally, after encapsulation into liposomes. Although they represent an improvement over the prior art, oral liposome formulations have been criticized because of their instability, leakage and potential destruction in gastric fluids.

The use of proliposomes represents an alternative to conventional liposomal formulations. Proliposomes are dry, free-flowing granular products, which, upon the addition of water, disperse to form a multilamellar liposomal suspension. The stability problems associated with conventional liposomes, including aggregation, susceptibility to hydrolysis and oxidation, may be avoided by using proliposomes. The use of proliposomes is well known in the pharmaceutical field.

Although the oral ingestion of drugs represents a safe and versatile method of pharmaceutical delivery, the therapeutic efficacy of many drugs is reduced because many pharmaceuticals are labile or inactivated under the acidic conditions of the stomach. Enteric coating materials have been applied to address this deficiency. Enteric coating materials are those that ensure that acid-labile drugs remain active in the stomach upon oral ingestion such that the active ingredient is released and absorbed in the intestine. Enteric coatings materials are well known in the pharmaceutical art and include alginates, alkali-soluble acrylic resins, hydroxypropyl methylcellulose phthalate, cellulose acetate phthalate, and the like.

Although the use of proliposomes and the use of enteric coatings are independently known in the art, the combination of an enteric coating with a proliposomal formulation has not been disclosed. Surprisingly, when an enteric coating of the current invention is combined with a proliposomal formulation of the current invention, drug delivery is enhanced. In many embodiments of the present invent, this novel and unexpected enhancement, which results from the unique combination of an enteric coating and a proliposomal formulation, relates to increased drug absorption, stability and bioavailablity.

In many embodiments of the current invention, the combination of an enteric coating and a proliposomal formulation overcomes the disadvantages of drug delivery systems known in the prior art. For example, the utility of previous systems for orally administering labile pharmacological substances has been limited by the need to use toxic amounts of delivery agents, the instability of the systems, the inability to protect the active ingredient, the inability to effectively deliver drugs that are poorly water soluble or labile, the inadequate shelf life of the systems, the failure of the drug delivery systems to promote absorption of the active agent and the difficulties inherent to manufacturing the systems.

SUMMARY OF THE INVENTION

The current invention relates to a drug delivery system comprising at least one pharmaceutically active agent, at least one phospholipid and an enteric coating material. A particular advantage of the current invention is that it provides a simple and inexpensive system to facilitate the oral administration of medicaments. In many embodiments, this drug delivery system enhances the stability and bioavailability of pharmaceutically active agents.

In one aspect of the invention, the pharmaceutically active agent is a poorly water soluble drug.

In another aspect of the invention, the phospholipid is distearoyl phosphatidylcholine, dipalmitoyl phosphatidylcholine or dimyristoyl phosphatidylcholine and the enteric coating material is cellulose acetate phthalate.

In another aspect of the invention, a pharmaceutical formulation is delivered in a tablet, capsule, suspension and/or liquid form. In alternative embodiments, carriers, diluents and/or lubricants are also included in the pharmaceutical formulation.

Another aspect of the invention relates to a method for making the drug delivery system comprising combining at least one pharmaceutically active agent with at least one phospholipid, and thereafter coating the combination with an enteric coating material. In alternate embodiments, pharmaceutically inactive agents, such as carriers, diluents and lubricants, are also included in the drug delivery system. Placebo may also be delivered according to certain embodiments of the invention.

A further aspect of the invention relates to a method for delivering a pharmaceutical formulation to a mammal by orally administering the formulation to the mammal. In specific embodiments, the current invention relates to preventing, diagnosing or treating an illness in a mammal with the drug delivery system of the present invention.

BRIEF DESCRIPTION OF THE DRAWINGS

FIG. 1 shows a comparison among dissolution rates of testosterone using various proliposomal formulations and pure testosterone.

FIG. 2 shows a comparison between dissolution rates of famotidine using a proliposomal formulation (DSPC) and pure famotidine.

DETAILED DESCRIPTION OF THE PREFERRED EMBODIMENT

Several embodiments of present invention relate to enteric coated proliposomal formulation comprising a pharmaceutically active agent, a phospholipid and an enteric coating material. In preferred embodiments, the enteric coated proliposomal (EnProLip™) formulation enhances the dissolution and bioavailability of drugs. The effect is more pronounced for drugs with extremely low water solubility, such as halofantrine and testosterone. A less pronounced rate of dissolution is observed with drugs with higher water solubilities, such as famotidine. In one embodiment, the current invention consists of a drug delivery system which provides a more rapid onset of drug action, a longer duration of action and an increased $C_{max}$ as compared to administration of the drug alone.

In a preferred embodiment, the formulation comprises
(a) a poorly water soluble drug;
(b) distearoyl phosphatidylcholine (DSPC), dipalmitoyl phosphatidylcholine (DPPC) or dimyristoyl phosphatidylcholine (DMPC); and
(c) cellulose acetate phthalate.

In one embodiment, the pharmaceutically active agent is a poorly water soluble drug. Poorly water soluble drugs are pharmaceutically active agents which require greater than approximately thirty (30) parts of solvent per one (1) part of solute to dissolve. Examples of poorly water drugs include, but are not limited to, griseofulvin, famotidine, meclizine, cyclosporine, carbamazipine, methotrexate, itraconazole, dipyridamole, mercaptopurine, halofantrine, amiodarone, lomustine, testosterone, misoprostil, etoposide, rifamycin, azathioprine, glyburide, tolbutamide, aminoglutethimide, taxol, clofibrate, nifedipine, methyldopa, ramipril, dicumarol, and the like. One skilled in the art will appreciate that this invention is not limited to poorly water soluble drugs but includes a wide range of pharmaceutically active and inactive agents. Drugs that are slightly soluble, sparingly soluble or hydrophilic may also be delivered using various embodiments of the present invention.

In a preferred embodiment, DSPC, DPPC or DMPC is used as the phospholipid. One skilled in the art will understand that other phospholipids, including, but not limited to, egg PC, soy PC, DMPG, DMPA, DPPG, DPPA, DSPG, DSPA, phosphatidylserine, sphigomyelin, and the like may be used.

In a preferred embodiment, cellulose acetate phthalate is used as the enteric coating. However, one skilled in the art will appreciate that alginates, alkali-soluble acrylic resins, hydroxypropyl methylcellulose phthalate, methacrylate-methacrylic acid coplymers, polyvinyl acetate phthalate, styrol maleic acid copolymers and the like may also be used. One skilled in the art will also appreciate that the enteric coating material used in various embodiments of the invention may include a combination of the aforementioned coatings.

In one embodiment of the invention, the enteric coated proliposome delivery system will be used for anti-emetic purposes by preventing the release of noxious ingredients in the stomach, thereby reducing nausea and other adverse side effects.

In another embodiment of the invention, the enteric coated proliposomal formulation is used to deliver drugs which are susceptible to degradation in the intestinal tract.

In another embodiment, the current invention will be used to administer drugs through various routes. The present invention will also be used to enhance delivery of drugs or other substances in the food industry, where enzyme immobilization is essential for various aspects of food processing.

In a further embodiment, the current invention will be used to treat a mammal comprising administering to the mammal a pharmaceutically active agent, a phospholipid and an enteric coating material.

One skilled in the art will understand that the current invention is not limited to the delivery of drugs or pharmaceutical agents. Any number of naturally occurring or synthetic substances, including diagnostic agents and therapeutic materials, may be delivered according to the current invention. These substances include, but are not limited to, anorexics, analgesics, antiarthritics, adrenergic blocking agents, steroids, vaccines, peptides, proteins, hormones, antibodies, antibiotics, antiviral agents, vitamins, nucleotides, nutritional agents, enzymes, genes, genetic material, cytotoxins, bacteria, microbes, viral agents, and the like. Placebo may also be administered using various embodiments of the current invention. Diluents, carriers, lubricants and the like, including, but not limited to, microcrystalline cellulose, starch, lactose, talc, mannitol, polyethylene glycol, polyvinylpyrrolidone, hydroxypropylmethyl cellulose, ethyl cellulose, fatty acids, fatty acid salts, glyceryl behenate, dextrose, dicalcium phosphate may also be administered using several embodiments of the present invention.

Further, one skilled in the art will understand that the amount of the active pharmaceutical or substance used in the current invention will depend on the dose required to be administered and the treatment desired. One skilled in the art will appreciate that "treatment" refers to any desired purpose for administering the pharmaceutically active ingredient, including prevention, control, cure, maintenance or improvement of health, and the like. By varying the concentration of the ingredients, size, number and/or amount of tablets, capsules, suspension or liquid, a wide range of doses may be orally administered. Time-released drugs may also be administered according to various embodiments of the present invention.

One skilled in the art will also appreciate that the current invention is not limited to the delivery of a single pharmaceutical agent. Indeed, more than one pharmaceutical agent may be delivered simultaneously using the current drug delivery system. For example, in one "dose", the recipient may receive a combination of two or more drugs, at least one drug and a carrier, etc.

In one embodiment of the invention, the drug delivery system is synthesized in the following manner: At least one pharmaceutically active agent and at least one phospholipid are dissolved in solvent at appropriate ratios and concentrations. Upon dissolution, the solvent is evaporated to yield a dry powder-like material. The dried material is passed through a sieve-like apparatus. This dried material is then coated with an enteric coating, which is preferably in solution and can be sprayed onto the dried material. The coated particles are then used to synthesize tablet, capsule or liquid preparations suitable for delivery to a mammal.

Several embodiments of the current invention are particularly advantageous because they allow for the enteric coating to be applied after the pharmaceutically active agent and phospholipid are mixed. This permits preparation of different forms of the formulation, including, tablets, capsules, suspensions, or liquids. Moreover, various embodiment of the present invention allow for the facile preparation of tablets of various sizes. The size of the tablets is preferably controlled by adjusting the pore size of the mesh or sieve.

I previously described a method for preparing drugs in a tablet or capsule form with an enteric coating. However, a particular advantage of various embodiments of the current invention is the ability to generate suspension or liquid forms of the formulation. Suspension or liquid forms are sometimes preferable because they do not affect gastrointestinal motility to the same extent as do capsules or tablets. For most drugs, it is important that that the pharmaceutically active compound is not eliminated in the gastrointestinal tract before it has had a chance to exert a localized effect or to pass into the bloodstream. When a formulation is in a suspension or liquid form, it is typically retained in the intestine for longer periods of time and, as such, absorption is increased as compared to capsules or tablets. Various aspects of this invention also provide for flexibility in the surface area of the formulation. Whereas tablets are generally restricted to a fixed surface area, several embodiments of the present invention permit the use of capsules, suspensions and liquids, which may provide a larger surface area and hence contribute to increased absorption and bioavailability.

I previously described a method for delivering drugs in which the drug was exposed to an aqueous phase. According to several embodiments of the current invention, the lipid and the drug are exposed to chloroform, or similar solvent. There is no exposure to an aqueous phase. For water sensitive drugs and drugs that are labile in water, such as antibodies, the absence of an initial aqueous phase preserves the integrity of these drugs. Further, because there is no exposure to an aqueous phase, liposomes are not formed. Hence, several embodiments of the current invention are directed to non-liposomal pharmaceutical formulations. As used herein, "non-liposomal" is defined as a formulation which is not exposed to an aqueous phase, and thus does not form liposomes, prior to the application of the enteric coating.

Not wishing to be bound by the following description, it is believed that various embodiments of the current invention work in the following manner: After formation of the proliposome formulation, the formulation is orally delivered to a mammal. When the proliposome formulation encounters an aqueous phase at a pH at or above approximately 7.0, liposomes are formed and the drug molecules are transported across the gastrointestinal membrane.

The following Examples illustrate various embodiments of the present invention and are not intended in any way to limit the invention.

EXAMPLE 1

Halofantrine and distearoyl phosphatidylcholine (1:3 ratio) were dissolved in chloroform and the solvent was evaporated using nitrogen gas. The dry powder was passed through a # 60 mesh screen. Cellulose acetate phthalate (50 mg) was dissolved in acetone (6 ml) and sprayed on the halofantrine and distearoyl phosphatidylcholine mixture.

Dissolution was carried out using 40 mg of the formulation using a Type II USP dissolution apparatus. The dissolution medium (250 ml) was phosphate buffered saline (pH 7.4). The temperature of the dissolution media was maintained at 37 ±0.5° C. and the rotation of the paddle was set at 50 rpm. Samples (5 ml) were withdrawn at 5, 10, 15, 30, 45, 60, 90, 120, 180 and 240 minutes. Equal volumes of phosphate buffered saline were added to maintain a constant volume of dissolution media.

The samples were analyzed by high performance liquid chromatography (HPLC). In the mobile phase, 46.5:53.5 (0.025 M potassium phosphate/sulfuric acid/triethylamine solution):acetonitrile was combined, mixed and filtered using a Kontes filter apparatus. Sodium dodecyl sulfate (1.1 g/L of mobile phase) was added to the filtered solution.

The parameters of the assay procedure was as follows. The flow rate was set at 1.2 ml/minute. The temperature was ambient. The run time was 30 minutes. The ultraviolet light detector was set at a wavelength of 254 nm. The retention times for (+) halofantrine and (−) halofantrine were 25 minutes and 28 minutes respectively.

The pharmacokinetic parameters of the enteric coated proliposomal formulation of halofantrine were evaluated as follows. The proliposomal product was prepared as a suspension in 0.78% methylcellulose. A non-liposomal suspension formulation (control) was prepared by dispersing halofantrine powder in 1% methylcellulose. Sprague-Dawley rats were cannulated at the right jugular vein under halothane anesthesia. After an overnight rest, the rats were given 7 mg/kg of a halofantrine suspension as either the proliposomal (7 rats) or control (6 rats) formulation by oral gavage. Serial blood samples were obtained from the cannula until 48 h post-dose. A stereospecific HPLC assay was used to measure plasma concentration of halofantrine enantiomers. Noncompartmental pharmacokinetic methods were used to determine $AUC_{0-24}$, $C_{max}$ and $t_{max}$. Student's unpaired t-test was used to assess significance of differences. Results (mean±SD) are provided in Table 1.

TABLE 1

Pharmacokinetic Results of the Halofantrine Study

| | AUC, μg × h/mL | | Cmax, ng/mL | | Tmax, h | |
|---|---|---|---|---|---|---|
| | Control | Liposome | Control | Liposome | Control | Liposome |
| (+)-HF | 5.2 ± 0.81[b] | 7.7 ± 1.8[a,b] | 391 ± 59.2[b] | 722 ± 170[a,b] | 7.0 ± 2.8 | 4.1 ± 2.3 |
| (−)-HF | 1.9 ± 0.53 | 2.6 ± 0.66[a] | 196 ± 42.3 | 360 ± 80.5[a] | 4.6 ± 2.1 | 4.0 ± 1.3 |

[a] = p < 0.05 compared to control;
[b] = p < 0.05 compared to antipode

The proliposomal formulation displayed higher bioavailability of both enantiomers than did the control formulation. The AUC and $C_{max}$ of halofnatrine enantiomers increased by over 40% and 80%, respectively. Although the mean tmax was lower for both enantiomers in the proliposomal formulation, the differences from control were not statistically significant.

EXAMPLE 2

Testosterone and phospholipid (DMPC, DPPC or DSPC; 1:1 ratio) were dissolved in chloroform. Chloroform was evaporated using nitrogen gas. The dry powder was passed using a # 60 mesh sieve. Cellulose acetate phthalate (40 mg) was dissolved in acetone (5 ml) and the resulting solution was sprayed on the solid dispersion containing the testosterone and phospholipid. Nitrogen gas was used to dry the powder.

Dissolution was carried out using 45 mg of the formulation using a Type II USP dissolution apparatus. The dissolution medium (300 ml) was phosphate buffered saline (pH 7.4). The temperature of the dissolution media was maintained at 37 ±0.5° C. and rotation of the paddle was set at 50 rpm. The samples (5 ml) were withdrawn at 2, 5, 8, 10, 15, 20, 25, 30, 40, 50, 60, 80, 100, and 120 minutes. Equal volumes of phosphate buffered saline were added to maintain a constant volume of dissolution media. Dissolution samples were analyzed by measuring the absorbance at 254 nm.

The rate and extent of dissolution of testosterone was significantly greater with all proliposomal formulations as compared to pure testosterone as shown in FIG. 2. The extent of dissolution was highest with the proliposomal formulation containing DMPC, followed by DSPC and DPPC. This may be explained by the phase transition temperature (Tc) of these lipids. DPPC has a Tc of 41° C., which is very close to the temperature of the dissolution study (37° C.). DMPC and DSPC have Tc's of 23° C. and 56° C. respectively. DMPC exists in a fluid state and DSPC in a gel state at 37° C. Because the Tc of DPPC was similar to the temperature of the dissolution study, the formulation may have been unstable, thus hampering the dissolution of testosterone. Nonetheless, the data indicates that the rate and extent of dissolution of testosterone was increased by using the enteric coated proliposomal formulation.

EXAMPLE 3

Famotidine and distearoyl phosphatidylcholine (DSPC; 1:3 ratio) were dissolved in chloroform. Chloroform was evaporated using nitrogen gas. The dry powder was passed using a # 60 mesh sieve. Cellulose acetate phthalate (50 mg) was dissolved in acetone (5 ml) and the resulting solution was sprayed on the solid dispersion containing testosterone and phospholipid. Nitrogen gas was used to dry the powder.

Dissolution was carried out using 87 mg of the formulation using a Type II USP dissolution apparatus. The dissolution medium (300 ml) was phosphate buffered saline (pH 7.4). The temperature of the dissolution media was maintained at 37 ±0.5° C. and the paddle rotation was set at 50 rpm. The samples (5 ml) were withdrawn at 2, 5, 8, 10, 15, 20, 25, 30, 40, 50, 60, 80, 100, and 120 minutes. Equal volumes of phosphate buffered saline were added to maintain a constant volume of dissolution media. Dissolution samples were analyzed by measuring the absorbance at 285 nm.

The rate of dissolution of famotidine formulation was significantly greater than pure famotidine. However, there was no significant increase in the extent of dissolution of famotidine in PBS. Because the proliposomal formulation results in a faster rate of dissolution, the onset of drug action will be more rapid.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A method of making a granular pharmaceutical product consisting essentially of:
    combining at least one lipophilic pharmaceutically active agent with at least one phospholipid in a non-aqueous solvent wherein said pharmaceutically active agent is a poorly water soluble drug;
    evaporating said non-aqueous solvent to produce a powder; and
    applying an enteric coating material to said powder to produce a granular product, wherein said enteric coating is in contact with at least a portion of said powder; and
    forming said coated granular product into a dosage form selected from the group consisting of one or more of the following: a capsule, suspension and tablet.

2. The method of claim 1, wherein said pharmaceutically active agent is selected from the group consisting of one or more of the following: famotidine, halofantrine, testosterone, and glyburide.

3. The method of claim 1, wherein said phospholipid is a pliosphatidyl phospholipid.

4. The method of claim 1, wherein said phospholipid is selected from the group consisting of one or more of the following: distearoyl phosphatidylcholine, dipalmitoyl phosphatidylcholine, dimyristoyl phosphatidylcholine, egg PC, soy PC, DMPG, DMPA, DPPG, DPPA, DSPG, DSPA, phosphatidylserine and sphigomyelin.

5. The method of claim 1, wherein said enteric coating material is selected from the group consisting of one or more of the following: cellulose acetate phthalate, alginates, alkali-soluble acrylic resins, hydroxypropyl methylcellulose phthalate, methacrylate-methacrylic acid coplymers, polyvinyl acetate phthalate and styrol maleic acid copolymers.

6. The method of claim 1, wherein said applying an enteric coating material comprises spraying said powder with said enteric coating material.

7. A method for delivering the pharmaceutical formulation produced by the method of claim 1 to a mammal comprising orally administering said granular pharmaceutical product to said mammal.

8. A method for diagnosing or treating an illness in a mammal comprising administering the granular pharmaceutical product produced by the method of claim 1.

9. The method of claim 8, wherein said granular pharmaceutical product is administered at a biologically active dose.

10. The method of claim 8, wherein said granular pharmaceutical product forms liposomes in the mammal's gastrointestinal tract.

* * * * *

UNITED STATES PATENT AND TRADEMARK OFFICE
CERTIFICATE OF CORRECTION

PATENT NO. : 6,759,058 B1
DATED : July 6, 2004
INVENTOR(S) : Guru V. Betageri

It is certified that error appears in the above-identified patent and that said Letters Patent is hereby corrected as shown below:

Column 7,
Line 44, after "solvent", insert -- , --.

Column 8,
Line 15, delete "pliosphatidyl" and insert -- phosphatidyl --.

Signed and Sealed this

Twenty-second Day of November, 2005

JON W. DUDAS
*Director of the United States Patent and Trademark Office*